(12) United States Patent
Sorrenti et al.

(10) Patent No.: US 10,758,390 B2
(45) Date of Patent: Sep. 1, 2020

(54) JOINT FOR REHABILITATION DEVICE

(71) Applicant: Ossur Iceland ehf, Reykjavik (IS)

(72) Inventors: Mark Sorrenti, Reykjavik (IS); Samiul Sorrenti, Reykjavik (IS); Andrew Hughes, Reykjavik (IS); Richard Genga, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 432 days.

(21) Appl. No.: 15/850,423

(22) Filed: Dec. 21, 2017

(65) Prior Publication Data
US 2018/0110642 A1   Apr. 26, 2018

Related U.S. Application Data

(63) Continuation of application No. 14/377,268, filed as application No. PCT/AU2013/000107 on Feb. 7, 2013, now Pat. No. 9,872,789.
(Continued)

(30) Foreign Application Priority Data

Jun. 29, 2012   (AU) ................................ 2012902800

(51) Int. Cl.
*A61F 5/01* (2006.01)
*A63B 21/00* (2006.01)
(Continued)

(52) U.S. Cl.
CPC ............ *A61F 5/0102* (2013.01); *A61F 5/013* (2013.01); *A61F 5/0123* (2013.01);
(Continued)

(58) Field of Classification Search
CPC ........ A61F 5/01; A61F 5/0102; A61F 5/0123; A61F 5/0125; A61F 2005/0132;
(Continued)

(56) References Cited

U.S. PATENT DOCUMENTS

| | | |
|---|---|---|
| 1,072,369 A | 9/1913 | Spahn et al. |
| 1,939,097 A | 12/1933 | Bauman |

(Continued)

FOREIGN PATENT DOCUMENTS

| | | |
|---|---|---|
| DE | 3501963 A1 | 7/1986 |
| GB | 813501 A | 5/1959 |

(Continued)

OTHER PUBLICATIONS

Extended European Search Report from EP Application No. EP 13747004, dated Jan. 5, 2016.
(Continued)

*Primary Examiner* — Tarla R Patel
(74) *Attorney, Agent, or Firm* — Workman Nydegger (57) ABSTRACT

A joint for a rehabilitation device and a rehabilitation device are disclosed. The joint is defined for operation between an end of a first member and an end of a second member. The joint enables the second member to pivot at the joint with respect to the first member. The joint includes a positioning mechanism for defining a set position from which the second member pivots. The joint also includes a restriction mechanism for restricting the degree of pivoting of the second member, from the set position. The joint further includes a biasing mechanism for biasing the second member such that it returns to the set position when an opposing force applied to the second member is less than the bias of the biasing mechanism. When the joint is in the set position, the biasing mechanism is configured such that no bias is applied to the second member.

16 Claims, 6 Drawing Sheets

Related U.S. Application Data (60) Provisional application No. 61/596,152, filed on Feb. 7, 2012.

(51) Int. Cl.
  *A63B 21/02* (2006.01)
  *A63B 21/04* (2006.01)
  *A63B 23/04* (2006.01)
  *A63B 23/08* (2006.01)
  *A63B 23/12* (2006.01)
  *A63B 23/035* (2006.01)
  *A63B 22/00* (2006.01)

(52) U.S. Cl.
  CPC ........ *A63B 21/025* (2013.01); *A63B 21/0421* (2013.01); *A63B 21/15* (2013.01); *A63B 21/4005* (2015.10); *A63B 21/4011* (2015.10); *A63B 21/4017* (2015.10); *A63B 21/4025* (2015.10); *A63B 21/4047* (2015.10); *A63B 23/03508* (2013.01); *A63B 23/0494* (2013.01); *A63B 23/08* (2013.01); *A63B 23/1245* (2013.01); *A63B 23/1272* (2013.01); *A61F 2005/0141* (2013.01); *A61F 2005/0158* (2013.01); *A61F 2005/0165* (2013.01); *A61F 2005/0167* (2013.01); *A61F 2005/0179* (2013.01); *A63B 23/0355* (2013.01); *A63B 2022/0094* (2013.01)

(58) Field of Classification Search
  CPC ...... A61F 2005/0141; A61F 2005/0165; A61F 2005/0167; A61F 2005/0158; A61F 2005/0179; A61F 5/013; A61F 23/0355; Y10T 16/5355; Y10T 16/53828; Y10T 16/541; Y10T 16/544; Y10T 16/5488; Y10T 16/551; Y10T 16/5513; Y10T 16/5515; A63B 23/03508; A63B 23/1272; A63B 21/4047; A63B 21/4025; A63B 21/4005; A63B 21/4017; A63B 21/4011; A63B 21/15; A63B 21/025; A63B 23/1245; A63B 23/08; A63B 21/0421; A63B 23/0494; A63B 2022/0094
  See application file for complete search history.

(56) References Cited

U.S. PATENT DOCUMENTS

| | | |
|---|---|---|
| 2,267,848 A | 12/1941 | Taylor |
| 2,410,560 A | 11/1946 | Witte |
| 2,536,454 A | 1/1951 | McIntyre |
| 2,567,195 A | 9/1951 | Ellery |
| 2,632,440 A | 3/1953 | Hauser et al. |
| 2,883,982 A | 4/1959 | Rainey |
| 3,528,412 A | 9/1970 | McDavid |
| 3,732,861 A | 5/1973 | Lehneis |
| 3,779,654 A | 12/1973 | Horne |
| 3,853,123 A | 12/1974 | Moore |
| 3,935,858 A | 2/1976 | Harroff |
| 4,064,874 A | 12/1977 | Valin |
| 4,088,130 A | 5/1978 | Applegate |
| 4,144,881 A | 3/1979 | Chappell |
| 4,254,950 A | 3/1981 | Baumann |
| 4,370,977 A | 2/1983 | Mauldin et al. |
| 4,915,098 A | 4/1990 | Young et al. |
| 5,052,379 A | 10/1991 | Airy et al. |
| 5,213,094 A | 5/1993 | Bonutti |
| 5,399,154 A | 3/1995 | Kipnis et al. |
| 5,437,619 A | 8/1995 | Malewicz et al. |
| 5,520,625 A * | 5/1996 | Malewicz ............ A61F 5/0125 602/16 |
| 5,658,241 A | 8/1997 | Deharde et al. |
| 5,683,353 A | 11/1997 | Hamersly |
| 5,759,165 A | 6/1998 | Malewicz |
| 5,954,677 A * | 9/1999 | Albrecht ............ A61F 5/0125 602/16 |
| 5,997,493 A | 12/1999 | Young |
| 2003/0149386 A1 | 8/2003 | Ceriani et al. |
| 2004/0049291 A1 | 3/2004 | Deharde et al. |
| 2004/0153016 A1* | 8/2004 | Salmon ............ A61F 5/0125 602/16 |
| 2007/0270976 A1 | 11/2007 | Deharde et al. |
| 2008/0249438 A1 | 10/2008 | Agrawal et al. |
| 2010/0022929 A1* | 1/2010 | Pansiera ............ A61F 5/0123 602/16 |
| 2010/0049108 A1* | 2/2010 | Napholz ............ A61F 5/0123 602/16 |
| 2010/0144492 A1 | 6/2010 | Ruan |
| 2011/0009786 A1 | 1/2011 | Chan |
| 2011/0021962 A1 | 1/2011 | Sorrenti |
| 2011/0251539 A1 | 10/2011 | Gentz et al. |
| 2012/0101420 A1 | 4/2012 | Albrecht et al. |
| 2012/0184880 A1* | 7/2012 | Doyle ............ A61H 1/0274 601/33 |
| 2014/0308065 A1 | 10/2014 | Deharde |
| 2015/0374532 A1 | 12/2015 | Fedon |

FOREIGN PATENT DOCUMENTS

| | | |
|---|---|---|
| GB | 2472036 | 1/2011 |
| WO | 9525489 A1 | 9/1995 |
| WO | 2012014164 A2 | 2/2012 |

OTHER PUBLICATIONS

International Search Report from PCT Application No. PCT/AU2013/000107, dated Mar. 28, 2013.
International Type Search Report from International Application No. 2012902800, dated Aug. 31, 2012.
Patent Examination Report from AU Application No. 2013204718, dated May 5, 2014.

* cited by examiner

JOINT FOR REHABILITATION DEVICE

This application claims priority to U.S. patent application Ser. No. 14/377,268 filed Aug. 7, 2014, which claims priority to International Application No. PCT/AU2013/000107 filed Feb. 7, 2013; U.S. Patent Application 61/596,152 filed Feb. 7, 2012; and Australian Patent Appln. No. 2012902800 filed Jun. 29, 2012; the entire contents of each are incorporated herein by reference.

TECHNICAL FIELD

A joint for a rehabilitation device is disclosed. A rehabilitation device is also disclosed. The joint and rehabilitation device may be used in or as a brace or support for a shoulder or knee, however, the disclosure is to be broadly interpreted, in that the joint and rehabilitation device may be adapted for use in a brace or support for an ankle, elbow, wrist, foot, hip or other joint.

BACKGROUND

Rehabilitation devices, or braces, are used to support limbs and joints after injury or surgery. The braces are used to severely limit, if not prevent, movement of the limb or joint so as to reduce strain on the surrounding muscles, ligaments and tendons and thereby aid the healing process. For example, shoulder braces are used to support a person's arm in a raised position as treatment for weakness in, or injury of, the person's shoulder. However, immobilising limbs and joints in this way can lead to muscle weakness which may necessitate further rehabilitation of the limbs and joints once the brace is removed.

Braces are available for different limbs and joints, such as ankle, foot, knee, shoulder, elbow and wrist. Some braces also provide resistance to movement, or a restricted range of motion. However, it can be difficult to change or alter the resistance to movement or restricted range of motion settings of the brace.

The above references to the background art do not constitute an admission that the art forms a part of the common general knowledge of a person of ordinary skill in the art. The above references are also not intended to limit the application of the joint and rehabilitation device as disclosed herein.

SUMMARY

According to a first aspect, there is provided a joint for a rehabilitation device. The joint is defined for operation between an end of a first member and an end of a second member. The joint is further defined to enable the second member to pivot at the joint with respect to the first member. The joint comprises a positioning mechanism for defining a set position from which the second member pivots, with respect to the first member. The joint also comprises a restriction mechanism for restricting the degree of pivoting of the second member from the set position, with respect to the first member. The joint further comprises a biasing mechanism for biasing the second member such that it returns to the set position when an opposing force applied to the second member is less than the bias of the biasing mechanism. The joint being characterised in that, when it is in the set position, the biasing mechanism is configured such that no bias is applied to the second member.

The set position may correspond to a so-called 'safe angle', 'starting angle' or 'starting position', the position to which the rehabilitation device is resiliently biased to return to when no force is being applied to the system. The 'safe angle', 'starting angle' or 'starting position' may refer to the angle or position at which it is considered safe for the body joint being rehabilitated to be maintained at. This, in effect, may form one limit of the range of movement (or motion) of the second member, with respect to the first member, and prevents further movement of the second member beyond the set position. The restriction mechanism can be used to provide a further limitation of the amount or degree of pivoting which the second member can undertake. This then further restricts the range of movement that can be achieved by the body joint being rehabilitated. For example, the joint may be set to have a 'safe angle' (or set position) of 10°. The joint may also, for example, be set to restrict the movement of the second member to 5° from this 'safe angle'. As both the set position, via the positioning mechanism, and the degree of pivoting of the second member with respect to the first member, via the restriction mechanism, can be independently altered, a gradual increase in the range of motion of the body joint can be achieved, to prevent further injury of the joint or surrounding muscles. It should also be noted that the joint may be locked at the set position (i.e. there is no additional movement possible beyond the set position), so that the joint can be used in a rehabilitation device that is purely supportive.

The bias in the biasing mechanism can be altered, thus altering the amount of force or pressure that is required to be applied to the second member to obtain movement thereof with respect to the first member. However, when the joint is in the set position, the biasing mechanism is configured such that no bias is applied to the second member (i.e. there is no bias in the biasing mechanism, and the mechanism may be considered to be in a neutral state). As there is no bias in the biasing mechanism when at the set position, it allows the bias to be varied for a specific range of motion (i.e. the degree of pivoting of the second member, with respect to the first member, from the set point to the limit set by the restriction mechanism) of the joint, as opposed to the entire potential range/degree of movement of the joint (i.e. the maximum range of movement which would be available if no set position were set, and no restrictions on pivoting were imposed). This can allow a rehabilitative professional more control over the bias in the joint, and thus have greater control over the treatment options for the user of a rehabilitation device having such a joint. This can also prevent unexpected or sudden movement of the second member, in use, should the set or starting position be accidently reset to the furthest limit.

In an embodiment, the positioning mechanism comprises an intermediate component for location between the ends of the first and second members, and a clamping mechanism for urging the ends of the first and second members together to secure the intermediate component therebetween, to define the joint in use. The intermediate component may be configured, when the clamping mechanism defines the joint, to engage with the end of the first member when the second member is pivoted from the set position. The intermediate component may be further configured to interact with the second member at the set position when it is pivoted back to the set position to prevent further pivoting beyond the set position. In this regard, the intermediate component may act as a bearing on which the second member pivots.

In an embodiment, the joint may be configured such that, when the clamping mechanism is released, the intermediate component can be disengaged from the first member and then rotated, together with a pivoting of the second member with respect to the first member, to define a different set position when the clamping mechanism is reclamped.

Having the two parts of the joints, i.e. the first and second members, able to disengage from each other can assist in being able to alter the set position simply and easily, whilst ensuring that the biasing mechanism remains in a neutral state. This allows the bias to be operative only over the range of motion that has been defined, and not the total possible range of movement of the joint.

In an embodiment, the restriction mechanism may be positioned between the intermediate component and the second member such that a portion of the restriction mechanism abuts against a projection from the intermediate component to prevent further pivoting of the second member and thereby limit the range of pivoting of the second member with respect to the first member. The restriction mechanism may be in the form of a delimiter or a stop.

In an embodiment, the position of the restriction mechanism with respect to the second member may be adjustable by an adjustable element that is moveable with respect to the second member and so as to engage with the restriction mechanism. For example, the adjustable element may be a grub screw. This allows the range of motion (i.e. the degree of pivoting available to the second member, with respect to the first member, from the set position to the restricted or limited position) to be adjusted (i.e. increased) when the body joint is to be exercised, and for it to be limited (i.e. decreased) when the body joint is to be rested, or supported.

In an embodiment, the intermediate component may comprise a projection that enables the interaction with the second member. This projection may be the projection against which the restriction mechanism abuts, or may be a separate projection to assist with rotation of the intermediate component with the second member, when the first and second members are disengaged (i.e. they are unclamped).

In an embodiment, the second member may comprise a groove. The ends of the groove may define the extremes from a range of available set positions, with the groove being arranged to receive the projection from the intermediate component to move therealong. In this regard, when the joint is disengaged, the projection on the intermediate component will prevent the second member from further movement, when it contacts an end of the groove, thus defining the total overall range of movement of the joint. For example, the joint may be able to be moved within an overall range of 0° to 180°. When the joint is engaged (i.e. when it is clamped together), and a set position has been defined, the overall range of motion will be limited to how far the projection can move along the groove from the set position until it reaches the end of the groove. To further limit the range of motion, the restriction mechanism (for example, the grub screw) can be used to prevent movement of the projection in the groove of the second member.

In an embodiment, the clamping mechanism may be one of a screw; bolt and nut; or worm drive. The clamping mechanism is engaged (i.e. clamped) when the joint is in use.

In an embodiment, when the clamping mechanism is released, a spring may urge the intermediate component away from the first member to facilitate disengagement therefrom. In one form, the spring may be a compression spring, such as a wavy washer. When the clamping mechanism clamps the respective member ends together, the spring or wavy washer compresses between the intermediate component and the first member end. When the clamping mechanism is released, however, the spring or wavy washer expands, forcing an expansion gap between the first member end and the intermediate component. This allows the second member, and intermediate component, to be rotated with respect to the first member, to thus alter the set position.

In an embodiment, the joint may further comprise a gearing mechanism. The gearing mechanism may engage with and act on the biasing mechanism. Rotation of the gearing mechanism in one direction may cause it to increase bias in the biasing mechanism, and rotation of the gearing mechanism in the opposite direction may cause it to decrease bias in the biasing mechanism. The increase or decrease in bias of the biasing mechanism can thus be used to increase or decrease the resistance between the first and second members. This can alter the amount of force or pressure that is required to be applied to the second member to obtain movement thereof with respect to the first member.

Configuring the joint in this way allows the bias between the first and second members to be easily and simply adjusted, as required, during the rehabilitation of a joint, such as a shoulder joint. If, for example, the shoulder has recently been operated on, the bias in the biasing mechanism might be low, to allow the shoulder joint to be moved without additional pressure being applied to the joint. A few days to a week or longer after surgery, however, it may be beneficial to increase the bias in the biasing mechanism so that more pressure or opposing force needs to be applied, thus engaging and strengthening the muscles surrounding the shoulder joint to aid in rehabilitation of the joint.

Alternatively, the bias in the biasing mechanism may be used to bias the second member into a specific position in relation to the first member, thus effectively holding the affected joint (e.g. shoulder, ankle, etc) in an optimal recovery and/or recuperative position. As the joint and surrounding muscles begin to heal, the person using the rehabilitation device may use the bias of the second arm as a resistive force, to further strengthen said joint and muscles.

In an embodiment, the gearing mechanism may be one of: a worm I gear and drive; a sun and planet gear set; and a curved rack and pinion. The gearing mechanism can provide a mechanical advantage to apply bias to the biasing mechanism, and while preferably a worm gear and drive, other gearing mechanisms which provide said mechanical advantage are also considered to fall within the scope of the present disclosure. A worm gear and drive has an inherent inertia to movement in that, once rotated to a given rotational position to produce a given increase or decrease in bias, the worm gear/drive holds that position.

In an embodiment, when the gearing mechanism is a worm gear and drive, the worm gear engages the biasing mechanism. The worm drive causes the worm gear to rotate, thus applying torque to the biasing mechanism. Further, the worm drive may be positioned in an aperture that extends through part of the first member, with an end of the drive being exposed. The exposed worm drive end allows the bias in the biasing mechanism to be increased or decreased by simply turning the worm drive in the appropriate direction. A tool may be used to turn the worm drive. The tool may be a specially designed tool to allow access to the specific worm drive used in the joint, or it may be an existing tool such as an Allen key, screwdriver, pliers, multi-grips, or a spanner etc,. The exposed worm drive simplifies the modification of the bias of the joint for the rehabilitation device, allowing the bias to be altered while the rehabilitation device is in use.

In an embodiment, the joint may further comprise a translational component that the worm gear can cause to rotate. This translational component can in turn engage an end of the biasing mechanism to either increase or decrease bias therein. In this regard, an end of the biasing mechanism may not be in direct contact with the worm gear.

In an embodiment, the biasing mechanism may be a torsion spring, although other biasing mechanisms, such as leaf springs, balance springs, etc are also contemplated. An end of the spring may be positioned in a corresponding recess in the second member, while the other end of the spring may be attached to the gearing mechanism (e.g. the worm gear). As the worm gear is caused to rotate in one direction, the torsion in the spring increases. As the worm gear is caused to rotate in the opposite direction, the torsion in the spring decreases.

According to a second aspect, there is provided a rehabilitation device for location at a body joint. The device comprises first and second members and a joint. The joint is defined for operation between an end of the first member and a respective end of the second member. The joint enables the second member to pivot at the joint with respect to the first member. The joint comprises a positioning mechanism for defining a set position from which the second member pivots, with respect to the first member. The joint also comprises a restriction mechanism for restricting the degree of pivoting of the second member, from the set position, with respect to the first member. The joint further comprises a biasing mechanism for biasing the second member such that it returns to the set position when an opposing force applied to the second member is less than the bias of the biasing mechanism. The joint being characterised in that, when the joint is in the set position, the biasing mechanism is configured such that no bias is applied to the second member.

The joint of the second aspect may be otherwise as defined in the first aspect.

In an embodiment, the first and/or second member may further comprise a pivot point located intermediate its ends. Pivoting at the pivot point can enable the joint to be repositioned in relation to the body joint. Repositioning of the rehabilitation device joint in relation to a body joint allows a simple readjustment of the device so that it is more properly aligned with the body joint. This allows a single device to be used for a variety of body shapes, whilst ensuring that the device joint is correctly aligned with the body joint.

In one embodiment, the pivot point may be located proximal to the device joint. This can assist in ensuring the device joint is being correctly positioned with respect to a user's body joint.

According to a third aspect, there is provided a rehabilitation device for location at a body joint. The device comprises first and second members and a joint. The joint is defined for operation between an end of the first member and a respective end of the second member. The first and/or second member further comprises a pivot point located intermediate its ends. Pivoting of the end of the first and/or second member at the pivot point enables the joint to be repositioned in relation to the body joint. Repositioning of the rehabilitation device joint in relation to a body joint allows a simple readjustment of the device to be more properly aligned with the body joint. This allows a single device to be used for a variety of body shapes, whilst ensuring that the device joint is correctly aligned with the body joint.

In one embodiment, the pivot point may be located proximal to the joint.

The joint of the third aspect may otherwise be as defined in the first aspect.

BRIEF DESCRIPTION OF THE DRAWINGS

Notwithstanding any other forms which may fall within the scope of the joint and rehabilitation device as set forth in the Summary, specific embodiments will now be described, by way of example only, with reference to the accompanying drawings in which.

DETAILED DESCRIPTION OF SPECIFIC EMBODIMENTS

Figure 1A:
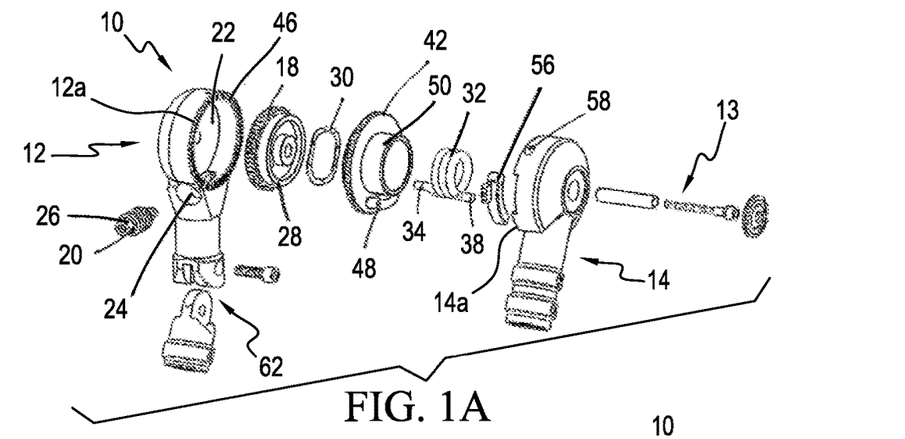
FIGS. 1A and 1B show exploded front and rear perspective views, respectively, of a joint for a rehabilitation device.
Figure 1B:
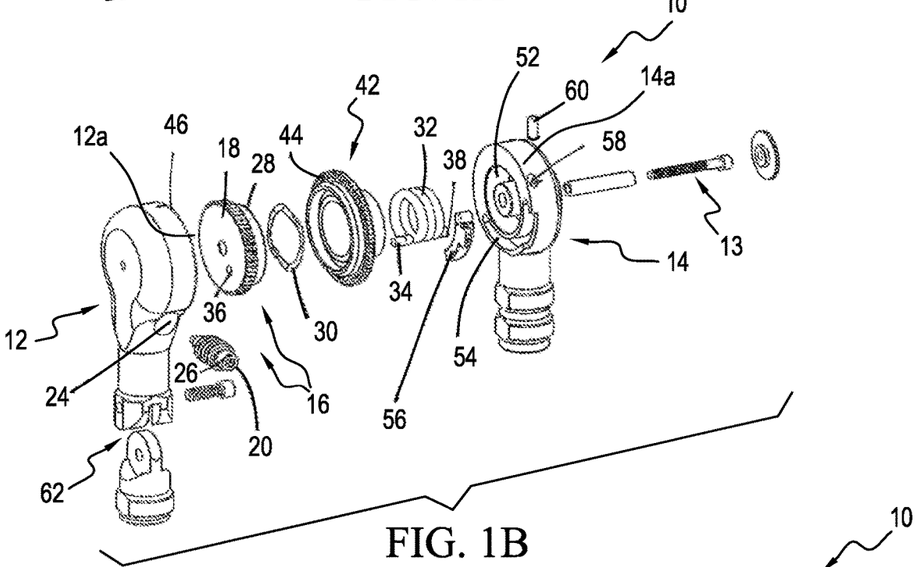
Figure 2:
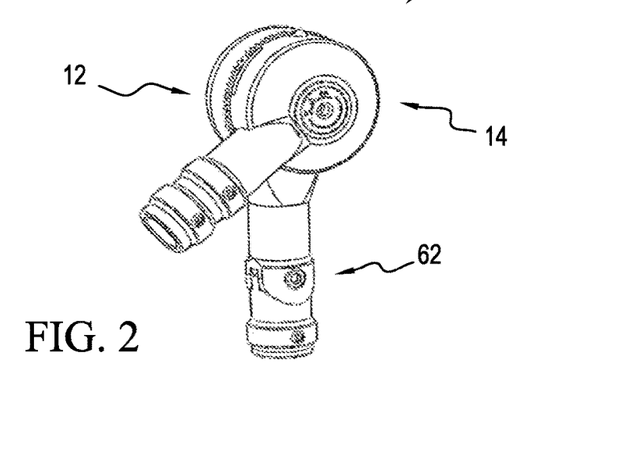
FIG. 2 shows a perspective view of the assembled joint shown in FIG. 1.
Figure 3:
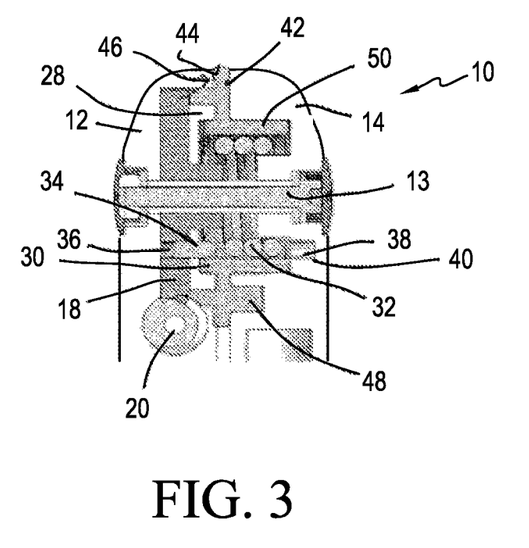
FIG. 3 shows a cross-sectional view of the joint shown in FIG. 2.
Figure 4:
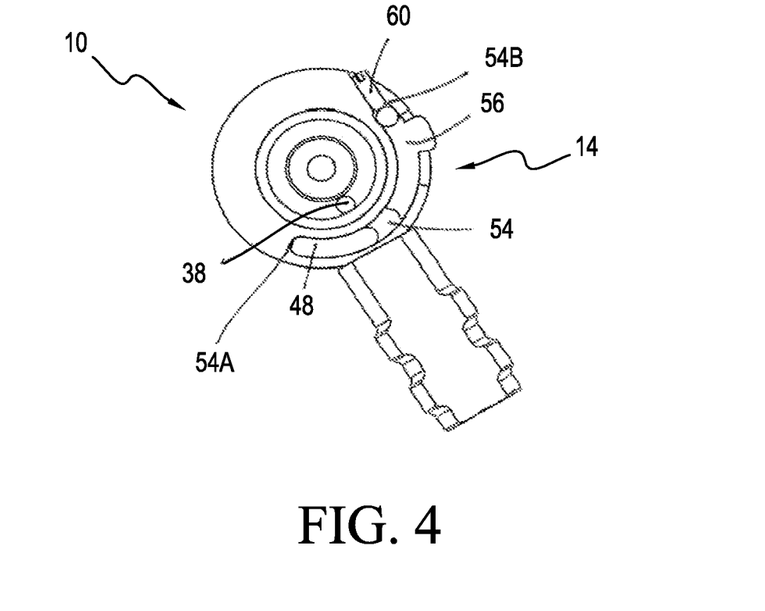
FIG. 4 shows a cross-sectional view through the front portion of the joint shown in FIG. 2.

Referring firstly to FIGS. 1A and 1B, front and rear exploded perspective views of an embodiment of a joint 10, for a rehabilitation device, are shown. The joint 10, shown assembled in FIG. 2, is defined for operation between a first member 12 having end 12a and a second member 14 having end 14a. The two member ends 12a, 14a are shown secured together by a clamping means, in the form of a screw 13. The first and second members 12, 14 may be in the form of arms used to support a body joint, and may extend in line with the bones of a limb, or along the torso, etc.

Joint 10 is shown having a gearing mechanism 16, in the form of a worm gear 18 and worm drive 20. First member 12 is shown having an internal cavity 22 on one side thereof to allow the worm gear 18 and worm drive 20 to be located therein. First member 12 is also shown having a channel 24 to allow a portion of the shaft 26 of the worm drive 20 to extend therefrom. This allows the worm drive 20 to be easily rotated, without the joint needing to be disassembled.

Joint 10 is also shown having an optional spacer element 28 positioned at worm gear 18 and a compression spring, in the form of a wavy washer, 30. The spacer element 28 acts as a housing for the wavy washer 30. A biasing mechanism, in the form of a torsion spring, 32 is also shown. One end 34 of the torsion spring 32 is located in an aperture 36 in worm gear 18, and the other end 38 of the torsion spring is located in an aperture 40 in the second member. In this embodiment, the end 34 of the torsion spring passes through an aperture in the spacer element 28 before locating in aperture 36 of the worm gear 18. The torsion in spring 32, when the joint 10 is assembled and clamped, can be increased or decreased by a simple turning of the worm drive 20. When worm drive 20 is turned in one direction, the worm gear 18 is caused to turn. As end 34 of the torsion spring 32 is attached thereto, this causes the end 34 to turn with the worm gear 18, thus increasing or decreasing the torsion in the spring 32, and thus the bias of the joint 10.

Joint 10 is further shown having an intermediate component, in the form of a ring, 42. Ring 42 is shown having a rim with a serrated edge face 44. This face 44 engages, or meshes, with a transposed finish on rim 46 of the first member 12. When joint 10 is clamped together, the serrations on edge face 44 mesh with those on rim 46, thus holding ring 42 stationary with respect to the first member 12. This allows the starting position (i.e. the set position, or safe angle) to be set. Further details of setting the starting position are provided, below. While ring 42 is shown having serrations on edge face 44 to mesh with rim 46, other mechanisms to secure the ring 42 to the first member when the joint 10 is in use are also possible. For example, the ring may include an alternative fastening mechanism such as an aperture with a grub screw. In this example, the grub screw would contact an outer edge of the first member and fasten the ring thereto.

Ring 42 is shown further having a projection 48, and a sleeve 50. When joint 10 is assembled, sleeve 50 is located in a corresponding cavity 52 in the second member 14, and acts as a sleeve bearing. In addition to cavity 52, second member 14 is also shown having a groove 54. When joint 10 is assembled, projection 48 of ring 42 is located in groove 54.

Joint 10 is also shown having a restriction mechanism, in the form of a range of motion (ROM) angle adjust cam, 56. Cam 56 is also located in groove 54 and moves freely therein. A bore 58 extends through the second member 14 to groove 54. An adjustable element, in the form of a grub screw, 60 may be threaded into bore 58 to limit the movement of cam 56 within groove 54.

When joint 10 is in use, with reference to FIGS. 2 to 5, the second member 14 moves with respect to the first member 12. The projection 48 of ring 42, which is secured to the first member 12, remains in a static position. When the second member 14 is moved, and the projection 48 abuts the end 54A of groove 54, the second member 14 is prevented from further downward pivoting or movement. Similarly, when the projection 48 abuts cam 56, both the cam 56 and projection 48 continue along the groove 54 until the cam 56 abuts the grub screw 60, or the other end 54B of the groove 54. When the grub screw 60 does not extend into the groove, a maximum range of motion can be achieved.

Joint 10 can also alter the 'resting position' of the second member 14 with respect to the first member 12. The position of the ring 42 and second member 14 can be altered by loosening the screw 13 which holds the first and second members 12, 14 together. The wavy washer 30 then expands and forces the serrated edge face 44 of ring 42 to disengage from the serrated rim 46 of the first member 12. The worm drive can then be turned, which causes the second member 14 to turn, as it is connected to end 38 of the torsion spring 32. Further, as the projection 48 is located in groove 54, the ring 42 is also caused to turn. As there is no load on the spring 32, these components will rotate together. When the suitable position is achieved, the screw 13 can be re-tightened, thus securing the new set position. When the two members 12, 14 are clamped together, turning the worm drive 20 will result in torsion either being increased or decreased in the spring 32. This alters the amount of pressure or force that is required to move the second member 14. This allows alteration of the pressure or force which is required by a body joint to move the second member, thus allowing the body joint to be exercised and strengthened after injury.

Figure 7:
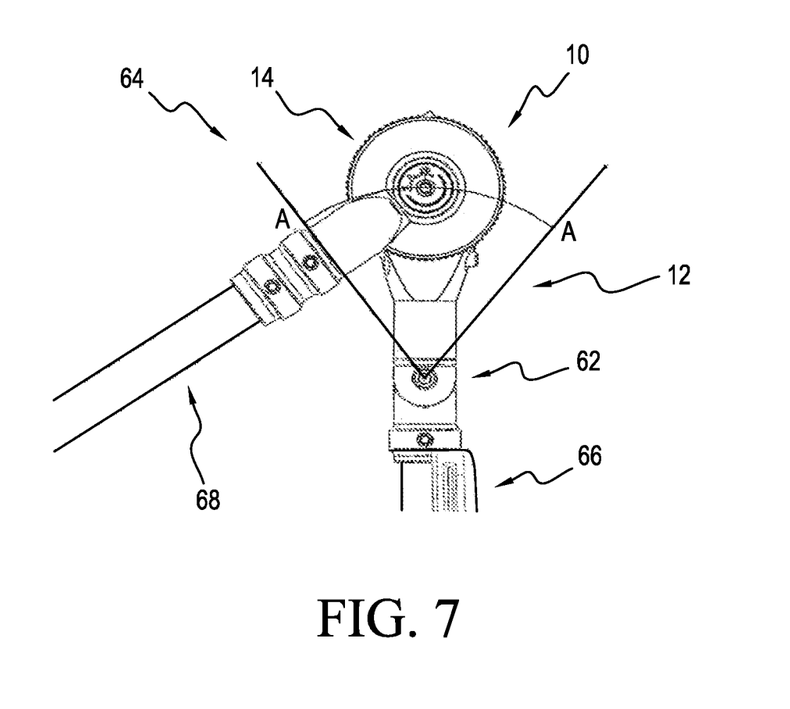
FIG. 7 shows the pivotable range of a joint in the shoulder rehabilitation device shown in FIGS. 5 and 6.

First member 12 is also shown having a pivot point 62 which allows the position of the joint 10 to be altered. With reference to FIG. 7, it can be seen that if the end 12a of the first member 12 (where the joint is located), is pivoted about the pivot point 62, that the joint can be repositioned along arc AA. This is useful, as users of the rehabilitation device may be of different shapes and sizes, thus allowing it to be customised and ensuring no additional strain is being placed on the body joint being rehabilitated.

Figure 5:
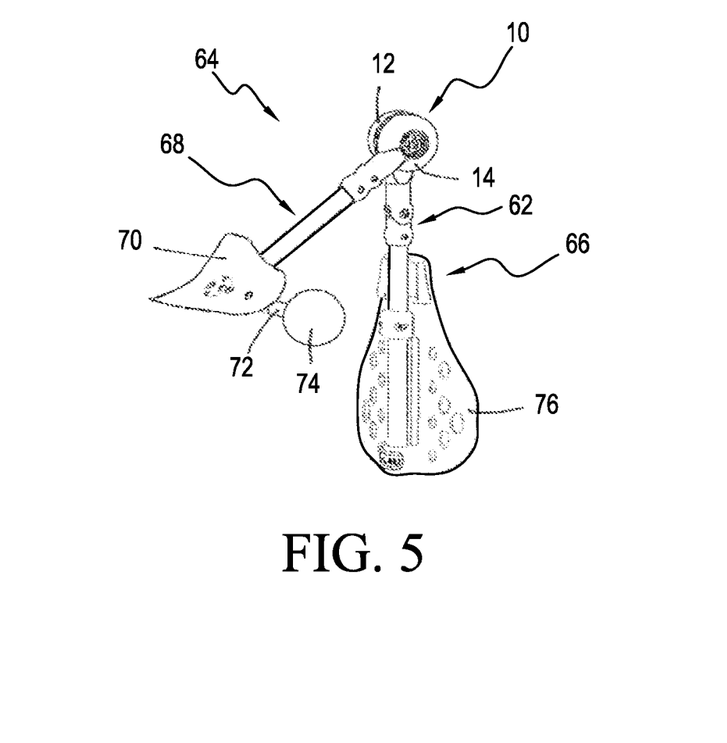
FIG. 5 shows a perspective view of a shoulder rehabilitation device.
Figure 6:
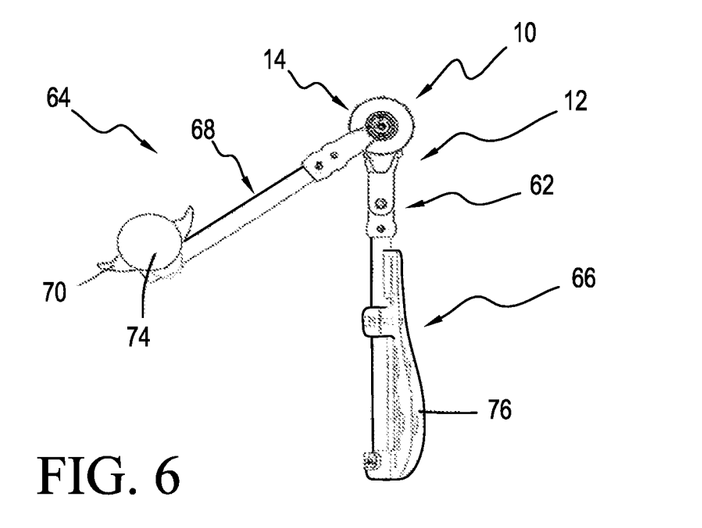
FIG. 6 shows a side view of the shoulder rehabilitation device shown in FIG. 5.

A rehabilitation device 64 in the form of a shoulder rehabilitative brace, suitable for use with a shoulder injury, is shown in FIGS. 5 to 7. It is shown having first and second arms 66, 68 which may be telescopically extendable or retractable. An arm rest 70 is also shown, and a third arm 72, having a spherical rest 74 for a user's wrist/hand. A torso plate 76 is also provided, to comfortably position the rehabilitative brace 64 against the user's torso and to distribute the weight of the brace. Straps, not shown, may be used to secure the device to the user's body. The rehabilitative brace 64 uses the joint 10, as described in relation to FIGS. 1 to 4.

Figure 8:
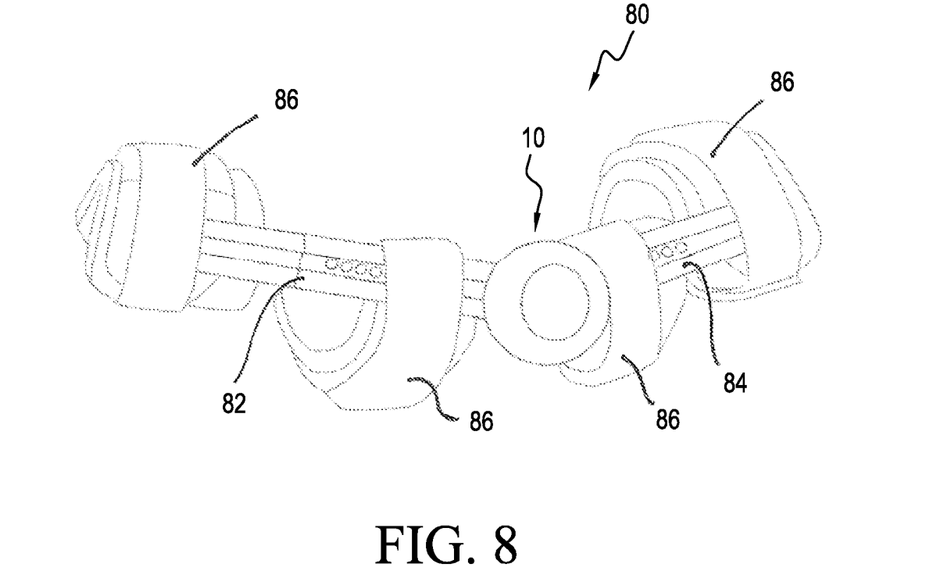
FIG. 8 shows a perspective view of an elbow rehabilitation device.

A rehabilitation device 80 in the form of an elbow rehabilitative brace, suitable for use with an elbow injury, is shown in FIG. 8. It is shown having first and second arms 82, 84 which may be telescopically extendable or retractable. Support regions and/or straps 86 are shown, so that the device can be secured to and support a user's arm and forearm. The rehabilitative brace 80 uses the joint 10, as described in relation to FIGS. 1 to 4, positioned between the first and second arms 82, 84.

Figure 9:
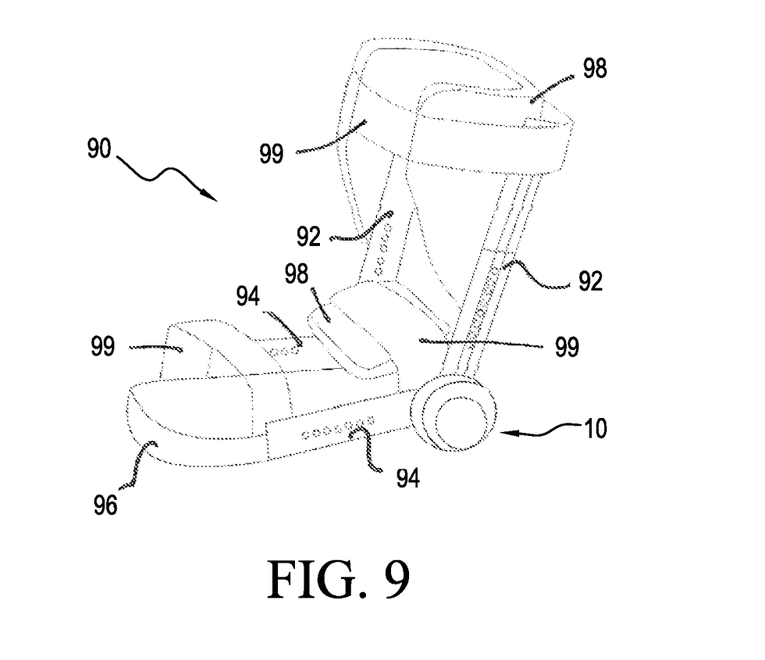
FIG. 9 shows a perspective view of a foot and/or ankle rehabilitation device.

A rehabilitation device 90 in the form of a foot/ankle rehabilitative brace, suitable for use with a foot or ankle injury, is shown in FIG. 9. It is shown having first and second arms 92, 94 extending on each side of the device which may be telescopically extendable or retractable. A support plate 96 is shown for supporting a user's foot, and the brace 90 is also shown having optional padded regions 98 for user comfort. Straps 99 are shown, so that the device can be secured to a user's lower leg and foot. The rehabilitative brace 90 uses joint 10, as described in relation to FIGS. 1 to 4, positioned between the first and second arms 92, 94. A similar arrangement of arms 92, 94 with joint 10 positioned therebetween is positioned on the other side of the device, although only one such arrangement can be seen. Alternatively, only one such arrangement may be employed in the brace 90.

Figure 10:
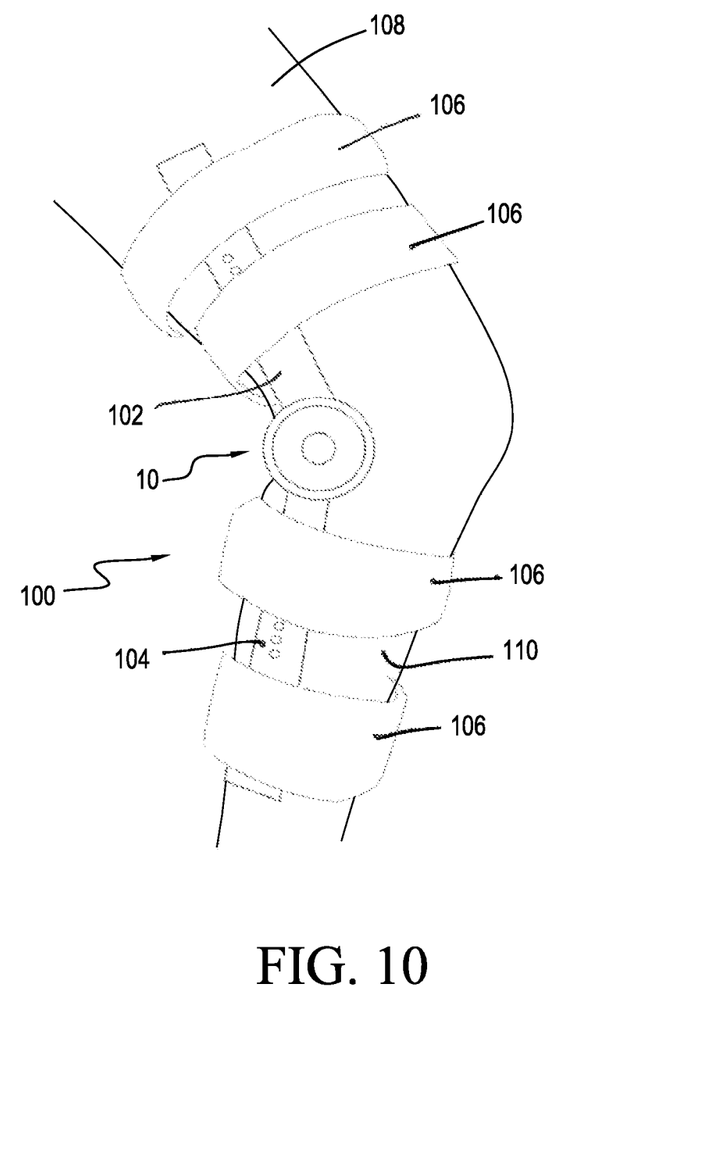
FIG. 10 shows a perspective view of a knee rehabilitation device.

A rehabilitation device 100 in the form of a knee rehabilitative brace, suitable for use with a knee injury, is shown in FIG. 10. It is shown having first and second arms 102, 104 which may be telescopically extendable or retractable. Straps 106 are provided, so that the device can be secured to a user's thigh 108 and leg 110 (i.e. the upper and lower portions of a leg). The straps 106 may be padded, for user comfort. The rehabilitative brace 100 uses the joint 10, as described in relation to FIGS. 1 to 4, positioned between the first and second arms 102, 104. The rehabilitation device 100 may include a similar arrangement of the arms 102, 104 and joint 10 for positioning on the opposite side of the user's leg.

Non-limiting Examples of the joint and rehabilitation device, in use, will now be described to illustrate how the joint and rehabilitation device may be applied, for example, for use in a shoulder brace/support and an elbow brace/support. It should, however, be appreciated that the joint and rehabilitation device can be used in a knee brace/support, an ankle (and/or foot) brace/support, etc.

Example 1

A shoulder rehabilitation device 64, such as the one described in relation to FIGS. 5 to 7, was strapped to a person's post-operative shoulder. Prior to strapping the rehabilitation device to the person, the range of motion and safe angles were respectively set at their minimums, to limit movement of the shoulder joint. First, the joint was undamped by unscrewing screw 13 to allow the ring 42 to be moved, and the projection 48 to be positioned at end 54A of groove 54. The joint was then reclamped by tightening screw 13. The range of motion was limited by screwing grub screw 60 into bore 58 as far as it could go, which effectively pushed cam 56 into contact with projection 48. This restricted any movement of the device.

The joint 10 of the rehabilitation device 64 was aligned with the glenohumeral joint of the person's shoulder by pivoting the end of the first member at the pivot point 62 and then locked in the appropriate position.

Some time after the operation, the range of motion was increased, to allow some use of the glenohumeral joint. The grub screw was unwound part of the way out of the bore. Bias was also added to the joint by turning the worm drive 20, which increased the torsion in the spring 32. This increased range of motion allowed the glenohumeral joint to be exercised, to strengthen the muscles surrounding it. The bias meant that the person had to apply more pressure to move the second arm. When the person's arm was not being exercised, the grub screw was screwed part way into the bore to limit the range of motion.

After some further time, the safe angle of the device joint was altered. This altered the position at which the person's arm was located in a resting position, again increasing use and strength in the shoulder muscles and joint. The safe angle was altered by loosening screw 13 and turning the worm drive 20, which moved the position of the ring 42, and retightening screw 13. The bias was again by turning the worm drive 20, which increased the torsion in the spring 32. As necessary, the range of motion was also altered, in the manner described above.

After approximately 6-8 weeks, the person's shoulder was rehabilitated sufficiently to remove the brace.

Example 2

An elbow rehabilitation device 80, such as the one described in relation to FIG. 8, was strapped to a person's injured elbow. Prior to strapping the rehabilitation device to the person, the range of motion and safe angles were respectively set, to limit movement of the elbow joint to a restricted range. First, the joint 10 was undamped by unscrewing screw 13 to allow the ring 42 to be moved, and the projection 48 to be positioned at end 54A of groove 54. The joint was then reclamped by tightening screw 13. The range of motion was limited by screwing grub screw 60 into bore 58, until a line on the screw which corresponded to 10 degrees, was aligned with the outer edge of bore 58. This restricted movement of the device to 10 degrees.

A week or so after starting to use the rehabilitation device 80, the range of motion was increased, to allow some use of the elbow joint. The grub screw was unwound so that a line thereon which indicated 20 degrees was aligned with the outer edge of the bore. Bias was also added to the joint by turning the worm drive 20, which added torsion to the spring 32. This increased range of motion allowed the elbow joint to be exercised, to strengthen the muscles surrounding it. The bias meant that the person had to apply more pressure to move the second arm. When the person's elbow was not being exercised, the grub screw was screwed part way into the bore to again limit the range of motion.

After some further time, the safe angle of the device joint was altered. This altered the position at which the person's elbow was located in a resting position, again increasing use and strength in the muscles surrounding the elbow and the elbow joint. The safe angle was altered by loosening screw 13 and turning the worm drive 20, which moved the position of the ring 42, and retightening screw 13. The bias was again added by turning the worm drive 20, which increased the torsion in the spring 32. As necessary, the range of motion was also altered, in the manner described above.

After approximately 3 weeks, the person's elbow was rehabilitated sufficiently to remove the brace.

Whilst a number of specific joint and rehabilitation device embodiments have been described, it should be appreciated that the joint and rehabilitation device may be embodied in many other forms. For example, the joint may comprise some or all of the features of the first aspect of the present disclosure, combined with known mechanisms to limit the range of motion of the device. Alternatively, the rehabilitation device may comprise some or all of the features of the joint disclosed in the first aspect of the present disclosure. Whilst the rehabilitation device, and joints for use therein, have been primarily described with reference to use as a shoulder brace or support, it would be appreciated by a person skilled in the art that the rehabilitation device, and joints for use therein, are also suitable for use in knee braces/supports, ankle braces/supports, elbow braces/supports, etc.

In the claims which follow, and in the preceding description, except where the context requires otherwise due to express language or necessary implication, the word "comprise" and variations such as "comprises" or "comprising" are used in an inclusive sense, i.e. to specify the presence of the stated features but not to preclude the presence or addition of further features in various embodiments of the joint and rehabilitation device as disclosed herein.

The invention claimed is:

1. A shoulder brace comprising:
    a torso plate;
    a first arm secured along the torso plate;
    a second arm;
    a joint secured to a first end of the first arm, and to a first end of the second arm, such that the first and second arms are pivotable relative to one another about the joint;
    an arm rest secured to a second end of the second arm wherein the joint includes a biasing mechanism for biasing the second arm relative to the first arm such that the second arm returns to a set position when an opposing force applied to the second arm is less than a bias of the biasing mechanism; a gearing mechanism connecting to the biasing mechanism such that adjustment of the gearing mechanism in a first direction increases the bias in the biasing mechanism, and adjustment of the gearing mechanism in a second direction decreases the bias in the biasing mechanism and wherein the biasing mechanism includes a spring having a first end engaging the gearing mechanism and a second end engaging a second member of the joint secured to the second arm, the spring passing through an aperture defined by a positioning mechanism.

2. The shoulder brace of claim 1, further comprising a third arm extending from the arm rest and having a spherical rest.

3. The shoulder brace of claim 1, further comprising at least one strap extending from the torso plate.

4. The shoulder brace of claim 1, wherein the first arm is telescopically extendable or retractable.

5. The shoulder brace of claim 1, wherein the second arm is telescopically extendable or retractable.

6. The shoulder brace of claim 1, wherein the joint is arranged for being unclamped for articulating the first arm relative to the second arm, and for being clamped to position the first arm relative to the second arm in a range of motion.

7. The shoulder brace of claim 1, wherein the joint includes a positioning mechanism for defining a set position from which the second arm pivots with respect to a first member of the joint secured to the first arm, the joint having a second member secured to the second arm.

8. The shoulder brace of claim 7 wherein the positioning mechanism comprises an intermediate component for location between ends of the first and second members, and a clamping mechanism for urging the ends of the first and second members together to secure the intermediate component therebetween to define the joint in use, the intermediate component being configured with an edge face, when the clamping mechanism defines the joint, to engage with the end of the first member to maintain the intermediate component to the first member in a stationary manner when the second member is pivoted from the set position, the intermediate component being further configured to interact with the second member at the set position when the second member is pivoted back to the set position relative to the intermediate component to prevent further pivoting beyond the set position.

9. The shoulder brace of claim 8, wherein the joint is configured such that, when the clamping mechanism is released, the intermediate component is able to be disengaged from the first member and then rotated, together with a pivoting of the second member with respect to the first member, to define a different set position when the clamping mechanism is reclamped.

10. The shoulder brace of claim 9, wherein the intermediate component comprises a projection that enables interaction between the second member and the intermediate component.

11. The shoulder brace of claim 10, wherein the second arm comprises a groove, ends of which define extremes from a range of available set positions, the groove being arranged to receive the projection from the intermediate component and to move therealong.

12. The shoulder brace of claim 9, wherein the clamping mechanism is one of a screw;
bolt and nut; or worm drive.

13. The shoulder brace of claim 8, wherein the joint includes a restriction mechanism for restricting a degree of pivoting of the second member from a set position with respect to the first member.

14. The shoulder brace of claim 13, wherein the restriction mechanism is positioned between the intermediate component and the second member such that a portion of the restriction mechanism abuts against a projection from the intermediate component to prevent further pivoting of the second member and to limit a range of pivoting of the second member with respect to the first member.

15. The shoulder brace of claim 13, wherein a position of the restriction mechanism with respect to the second member is adjustable by an adjustable element that is movable with respect to the second member and so as to engage with the restriction mechanism.

16. A method for using a shoulder brace, comprising the steps of:

securing a torso plate against a user, the torso plate carrying a first member secured along the torso plate, a joint connecting a first arm to a second arm;

unclamping the joint to arrange a range of motion between the first and second arms;

clamping the joint once the range of motion is established between the first and second arms;

aligning the joint with a glenohumeral joint of a shoulder of the user by pivoting the first member of the joint at a pivot point of the user and then locking the joint the steps of: after a range of motion of the glenohumeral joint of the user's shoulder is increased, adjusting a biasing mechanism for biasing a second member of the joint such that it returns to a set position when an opposing force applied to the second member is less than a bias of the biasing mechanism; adjusting a gearing mechanism connecting to the biasing mechanism such that adjustment of the gearing mechanism in a first direction increases the bias in the biasing mechanism, and adjustment of the gearing mechanism in a second direction decreases the bias in the biasing mechanism and wherein the biasing mechanism includes a spring having a first end engaging the gearing mechanism and a second end engaging the second member, the spring passing through an aperture defined by a positioning mechanism.

\* \* \* \* \*